United States Patent [19]
Dirks et al.

[11] 3,951,756
[45] Apr. 20, 1976

[54] PURIFICATION OF ALKYL ESTERS

[75] Inventors: Jerald Edson Dirks, Hastings, Nebr.; Gene Jordan Fisher, Corpus Christi, Tex.

[73] Assignee: Celanese Corporation, New York, N.Y.

[22] Filed: Nov. 8, 1974

[21] Appl. No.: 522,196

[52] U.S. Cl. ............................ 203/95; 203/4; 203/87; 203/DIG. 21; 202/182; 260/486 R
[51] Int. Cl.² .................. B01D 3/34; B01D 3/14; C07C 69/52
[58] Field of Search .......... 203/42, 95–98, 203/92, 93, 4, 49, 87, DIG. 21; 260/486 R, 499; 202/182

[56] References Cited
UNITED STATES PATENTS

| | | | |
|---|---|---|---|
| 1,929,901 | 10/1933 | Ricard et al. | 203/96 |
| 2,489,619 | 11/1949 | Carlson et al. | 203/98 |
| 2,980,730 | 4/1961 | Dobson | 203/98 |
| 3,420,751 | 1/1969 | Hougland et al. | 203/97 |
| 3,438,870 | 4/1969 | Roscher et al. | 260/499 |
| 3,458,406 | 7/1969 | Fisher et al. | 260/499 |
| 3,513,078 | 5/1970 | Biarnais et al. | 260/499 |
| 3,692,636 | 9/1972 | Huguet | 260/499 |
| 3,738,915 | 6/1973 | Fiore et al. | 203/98 |

*Primary Examiner*—Jack Sofer
*Attorney, Agent, or Firm*—Stewart N. Rice; Ralph M. Pritchett

[57] ABSTRACT

A distillation process for removing light ends impurities from alkyl esters of carboxylic acids wherein a purified ester is removed as residue, and wherein an inert gas and water are added to the overhead vapors from the distillation so as to facilitate separation of the light ends therefrom.

11 Claims, 1 Drawing Figure

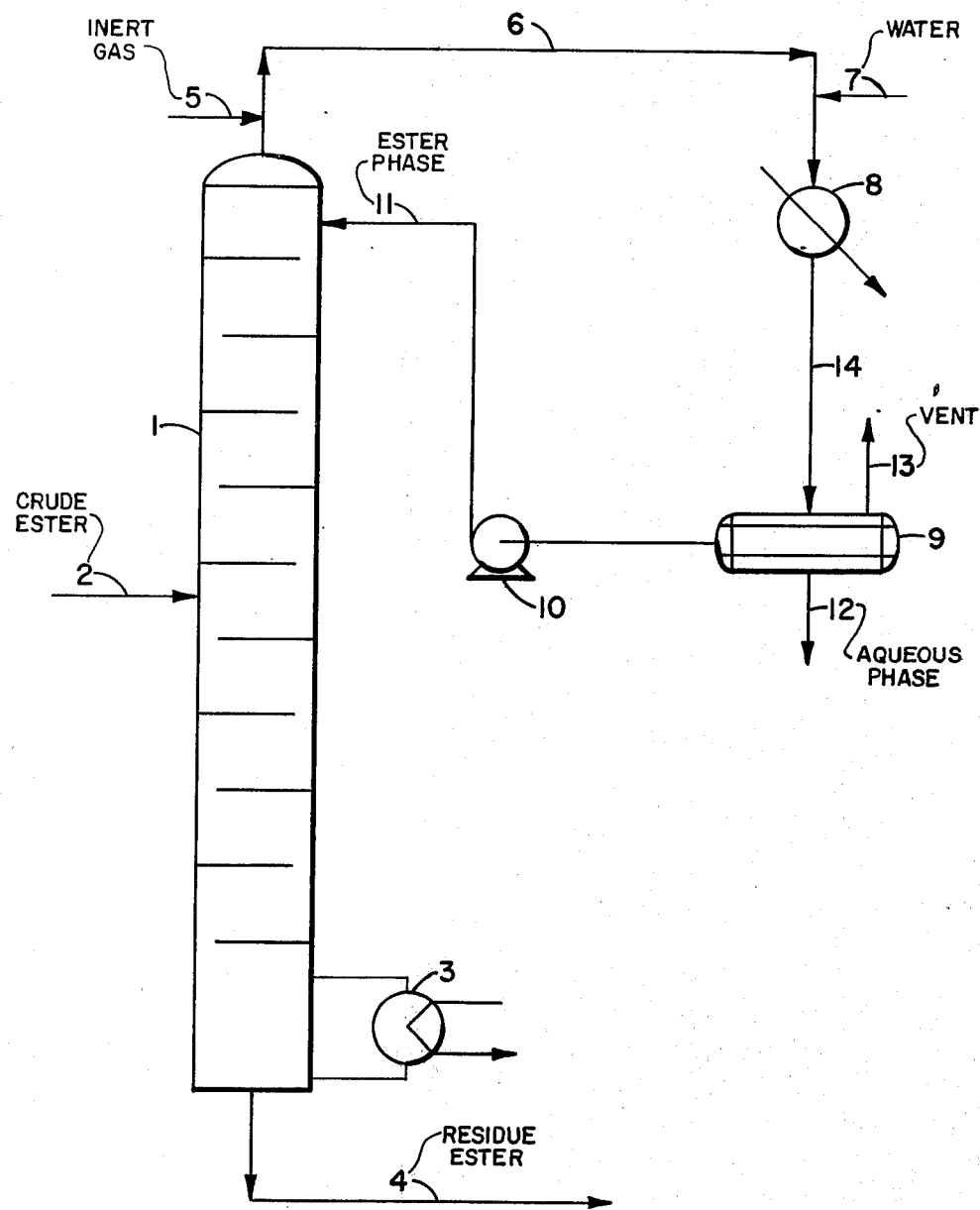

PURIFICATION OF ALKYL ESTERS

BACKGROUND OF THE INVENTION

Processes for the production of alkyl esters of monocarboxylic acids, e.g. ethyl acrylate, are well known in the art. Processes for such include direct esterification by reaction of an alkanol and the carboxylic acid as well as other processes such as those wherein esters of monounsaturated acids are produced by interacting the unsaturated acid with a monoolefin in the presence of sulfuric acid. Typical of such processes are those disclosed in U.S. Pat. No. 3,539,621 issued Nov. 10, 1970, to Cipollone et al. and U.S. Pat. No. 3,703,539 issued Nov. 21, 1972, to Di Liddo. Regardless of the process from which an ester is derived, the crude ester product will contain various light ends impurities which must be removed. Some of these light ends impurities are water soluble and some are water insoluble, with the particular impurities in any given crude ester depending on the method of production and purity of reactants. The various light ends impurities may be removed by conventional distillation; however, because of various possible azeotropes and mutual solubilities an excessively large distillation column is required in order to avoid product losses. Because of this, much time and effort is expended to discover new and useful methods for removing these light ends impurities.

It is thus an object of the present invention to provide a new and useful distillation process for removing light ends from crude alkyl esters of carboxylic acids. A particular object to the present invention is to provide a new and useful distillation method for efficiently removing light ends from a crude ethyl acrylate prepared by the interaction of ethylene and acrylic acid in the presence of sulfuric acid. Additional objects will become apparent from the following description of the following invention. In the following description and the claims, all parts and percentages are by weight unless otherwise specified.

SUMMARY

The foregoing and other objects are accomplished by the present invention, which in one of its aspects is a continuous distillation process for removal of water soluble and water insoluble light ends impurities from a crude lower alkyl ester of a monocarboxylic acid of 1 to 6 carbon atoms, which process comprises continuously; (a) passing crude ester as feed to a distillation zone which is operated so as to obtain a residue consisting of the said ester having less of said light ends impurities therein than said crude ester, and so as to obtain a distillate of overhead vapors containing light ends impurities; (b) adding to said overhead vapors an inert gas and water; (c) in a partial condenser cooling the combined stream so obtained by adding said inert gas and said water to said overhead vapors to a temperature sufficient to condense substantially all of the water and the said ester contained therein, but which temperature is high enough to cause the amount of said water insoluble light ends impurities contained in the hereafter defined vapor phase of the hereafter defined phase separator to at least 50% of the amount of said water insoluble light ends impurities contained in said feed to the distillation zone; and (d) passing the effluent from said partial condenser to a phase separator and allowing such to separate into a vapor phase, a liquid aqueous phase and liquid ester phase, and recycling said liquid ester phase back to the top of said distillation zone as reflux.

BRIEF DESCRIPTION OF THE DRAWING

The drawing is a schematic diagram of a distillation tower and associated equipment illustrating the distillation process of the present invention.

DETAILED DESCRIPTION OF THE INVENTION

The distillation process of the present invention is advantageously applied to treat any of the lower alkyl esters of the $C_1$-$C_6$ monocarboxylic acids, especially the lower alkyl esters of the ethylenically unsaturated monocarboxylic acids. By "lower alkyl" is meant an alkyl group of one to about three carbons such as methyl, ethyl, and isopropyl. The acid portion of the ester may be derived from acids such as formic, acetic, acrylic, propionic, methacrylic, pentanoic and vinylacetic (3-butenoic) acid. The esters may be represented by the formula $R_1COOR_2$ wherein $R_1$ is hydrogen, an alkyl group of 1 to 5 carbons or an alkenyl group of 1 to 5 carbons, and wherein $R_2$ (the alcohol moiety portion) is an alkyl group of 1 to 3 carbons. By "alkenyl" is meant a monoethylenically unsaturated, monovalent, hydrocarbon radical. Specific esters include methyl formate, ethyl acrylate, methyl acrylate, methyl methacrylate, ethyl acetate, ethyl propionate and ethyl caproate. The process is most suitable for purifying the alkyl esters of acrylic and methacrylic acid, especially those derived from the interaction of the acid, an alpha monoolefin and sulfuric acid. The crude ester which is treated according to the present invention may have undergone some purification steps prior to utilizing the present invention.

More specifically the present invention is useful in treating a crude ester containing less than 5% light ends impurities, e.g. 0.1 to 5.0% thereof. By "light ends impurities" is meant those which are more volatile, that is of a lower boiling point, than the particular ester being purified. The light ends will vary according to the method by which the ester was produced and according to the purity of the reactants. Some of the light ends will be water soluble and some water insoluble. When speaking herein of a "water soluble" or a "water insoluble" impurity, such is not meant to imply that the impurity is infinitely water soluble or absolutely water insoluble. Instead such terms are to mean substantially water soluble and substantially water insoluble. For example, ethyl acetate has a solubility of only about 8.6 grams per 100 milliliters of water at 20°C and is for purposes hereof considered water insoluble.

Regardless of the method by which the ester has been produced there will usually be water soluble impurities comprising alkyl alcohols wherein the alkyl group corresponds to the alkyl group of the alcohol moiety portion of the ester being purified; and there will usually be water insoluble impurities comprising dialkyl ethers wherein the alkyl groups correspond to the alkyl group of the alcohol moiety portions of the ester. Thus in a crude ethyl acrylate there will usually be ethyl alcohol and diethyl ether as impurities. There may also be various other light ends impurities such as other esters, water and sulfur dioxide. Sulfur dioxide is particularly likely to be present when treating an alkyl ester of an unsaturated acid such as ethyl acrylate derived from the interaction of an alpha monoolefin, an unsaturated acid and sulfuric acid. Ester impurities, that is esters which are other than the ester being purified, usually result from using an impure acid starting material in the esterification process which contains another acid as an impuritiy. Acrylic acid thus frequently contains acetic acid as an impurity such that acetic ester impurities will be formed when esterfying the acrylic acid. A typical crude ester will, for example, contain light ends comprising from about 0 to 2% sulfur dioxide, 0.01 to 3% dialkyl ether, 0.01 to 3% alkyl alcohol, 0 to 2% water and 0 to 3% of an alkyl ester impurity. Sulfur dioxide and ester impurities are considered to be substantially water insoluble for purposes hereof.

In order to more fully explain the present invention, reference is made to the drawing which illustrates a distillation tower 1 having associated therewith a reboiler 3, partial condenser 8, phase separator 9 and pump 10. The distillation tower and other associated equipment utilized to accomplish the present invention may be of conventional design although such is preferably constructed of stainless steel. The distillation tower may contain packing, such as Berl saddles or Raschig rings, or may contain plates, such as sieve plates, dualflo plates, valve trays and bubble-cap plates. Plates are preferred over packing. The distillation tower generally should contain the equivalent of at least 15 theoretical trays, e.g. the equivalent of 15 to 30 theoretical trays. The distillation zone is preferably operated at a pressure of about 0.5 to 2.0 atmospheres absolute.

Referring again to the drawing, the crude ester is fed to tower 1 through line 2, there being removed through line 4 a distillation residue which consists of the ester product of improved purity, preferably containing less than 0.05% light ends impurities. Overhead vapors removed through line 6 contain most of the light ends impurities fed to tower 1 as well as some of the desired ester product. Preferably the distillation is operated such that at least 50% of the light ends impurities contained in the crude ester feed to tower 1 end up in the overhead vapors, more preferably at least 70% thereof. The crude ester is advantageously fed to tower 1 such that there are the equivalent of at least about 10 theoretical trays below the feed point and at least about 5 theoretical trays above the feed point. The crude ethyl acrylate will thus usually be fed about two-thirds of the way up the distillation tower.

In a conventional distillation, the overhead vapors would be passed directly through partial condenser 8 thence through line 14 to phase separator 9 where a gas phase and a liquid phase would be allowed to form, with the liquid phase being pumped by means of pump 10 through line 11 to the top of the tower as reflux. It has been found that the efficiency of such a distillation can be appreciably increased by adding to the overhead vapors an inert gas through line 5 and water through line 7. Further, in accordance with the present invention, three phases will be allowed to form in phase separator 9, such phases being a gas phase, a liquid aqueous phase and a liquid ester phase. The aqueous phase will be the heavier of the three phases and will be removed through line 12, the gas phase will be the lightest of the three phases, and will be removed through line 13, and the ester phase which will be the upper liquid phase will be returned to the top of tower 1 through line 11 as reflux.

The inert gas added through line 5 may be any which is not reactive with itself or with the components of the overhead vapors, and which will remain as a vapor, under the temperatures and pressure conditions existing at the top of tower 1, in condenser 8 or in phase separator 9. The boiling point of the inert gas is preferably below −25°C at atmospheric pressure. Suitable inert gases include those selected from hydrocarbons, nitrogen, carbon dioxide, argon and helium. Where hydrocarbons are utilized such are preferably free of acetylenic unsaturation, suitable hydrocarbons including methane, ethane, propane, ethylene, and propylene. The amount of inert gas added to the overhead vapors should be at least 1.0 milliliters, as measured at standard temperature and pressure (STP), of inert gas per gram of feed to the tower, generally 1 to 50, and preferably 5 to 15 milliliters, measured at STP, per gram of tower feed.

The amount of water added through line 7 to the overhead vapors should be from 0.5 to 50% by weight of the weight of the feed to tower 1. The water may be added to the overhead vapors prior to or simultaneously with the addition of the inert gas instead of afterward. Preferably water in an amount of 1 to 10% weight of that of the tower feed is added. The water added may be in liquid form or in vapor form as steam, preferably vapor.

The partial condenser 8 should be operated at a temperature sufficient to condense substantially all, that is at least 90% and preferably at least 95%, of the water and the ester being purified which are contained in the combined stream passed to the partial condenser. However, the cooling should not be to a temperature so low as to cause the condensation of too many of the water insoluble light ends impurities. More specifically the cooling should not be so low as to cause the amount of water insoluble impurities in the gaseous vent stream removed from phase separator 9 through line 13 to be less than 50% of that being fed to the tower. In other words, the exit temperature of the partial condenser should be high enough to cause the amount of water insoluble light ends impurities in the gaseous vent stream to be at least 50% of the amount thereof in the tower feed. Thus if 100 grams per minute of water insoluble light ends impurities were being passed to tower 1 in the feed, then at least 50 grams per minute of such water insoluble impurities should be in the gaseous phase in the phase separator 9. The composition of the gaseous phase can easily be monitored and the amount of ccooling provided by the partial condenser regulated accordingly. Preferably the exit temperatures of partial condenser 8 is high enough to cause the amount of water insoluble light ends in the gaseous phase of the phase separator to be at least 70% of the amount thereof in the tower feed. When operating at substantially atmospheric pressure, the desired results can be accomplished in an ethyl acrylate purification by causing the stream exiting condenser 8 through line 14 to be at a temperature within the range of 10° to 50°C.

After being cooled, the combined stream is passed through line 14 to phase separator 9 where it is allowed to separate into three phases as stated above. The separator can be of conventional design and may advantageously contain baffles to facilitate separation. It has been found that addition of the inert gas to the overhead vapors will cause or aid in the removal of the lighter of the light ends, e.g. sulfur dioxide and dialkyl ethers, as components of the gaseous vent stream removed through line 13. In addition, where an ester impurity is present much of the ester impurity present in the overhead vapors will reside in the gaseous phase and be removed through line 13. Addition of the water to the overhead vapors serves to create an aqueous phase which will contain most of the alkyl alcohols and water present in the overhead vapors. The ester phase is recycled through line 11 and introduced at the upper end of distillation tower 1. In order to prevent a buildup of impurities, a periodic or continuous blowdown may be taken of the ester phase being recycled through line 11.

Although not shown on the drawing, the addition of a polymerization inhibitor to the system is generally desirable when purifying esters of unsaturated carboxylic acids. These inhibitors may advantageously be added to the overhead vapors prior to or after partial condenser 8 and can even be added to the material in reflux line 11. Preferably the inhibitor is added to the stream exiting the partial condenser, that is to line 14. Suitable inhibitors include hydroquinone, phenothiazine, quinone, methyl ether of hydroquinone and the like. In order to facilitate pumping of the inhibitor it is preferably added as a dilute solution of the ester being purified. Inhibitors may also be present in the feed to tower 1 and usually will be where esters of unsaturated acids are being purified. Practically all of the inhibitor passing to the system in the feed, or added to the overhead vapors, will eventually end up in the ester product removed through line 4 as residue from the distillation.

EXAMPLE

About 811 grams per hour of a crude ethyl acrylate containing 0.90% diethyl ether, 1.04% sulfur dioxide, 0.60% ethyl acetate, 0.50% ethanol, 1.0% water and 200 ppm phenothiazine inhibitor was treated in a distillation apparatus as illustrated in the drawing. Distillation column 1 consisted of 55 sieve trays with the feed through line 2 being introduced at the 35th tray from the bottom. The distillation column was operated at an overhead pressure of atmospheric, an overhead temperature of 67°C and a bottoms temperature of 102°C. The feed through line 2 was at room temperature and condenser 8 was maintained so to cool the material to the phase separator to about 25°C. About 11.1 grams per hour of nitrogen gas at room temperature was added to the overhead vapors through line 5 and about 15.1 grams per hour of liquid water at room temperature was added through line 7. Also added to line 14 was about 19 grams per hour at room temperature of an inhibitor stream composed of 99% ethyl acrylate and 1% hyroquinone.

Removed through line 4 was about 776 grams per hour of a purified ethyl acrylate product of above 99.9% purity. This ethyl acrylate product contained less than 2 ppm diethyl ether, less than 1 ppm sulfur dioxide, less than 3 ppm ethyl acetate, less than 20 ppm ethanol, less than 0.01% water, and practically all of the phenothiazine and hydroquinone fed to the system. Removed from phase separator 9 was vent stream (line 13) of about 27.7 grams per hour containing 0.9% ethyl acrylate, 19% diethyl ether, 25% sulfur dioxide, 14% ethyl acetate, 1.8% water and 40% nitrogen. About 26.5 grams per hour of aqueous phase was removed from phase separator 9 through line 12, the composition being about 0.47% ethyl acrylate, 0.9% diethyl ether, 0.7% sulfur dioxide, 2.8% ethyl acetate, 11.8% ethanol and 83.3% water. The reflux returned through line 11 consisted of about 1,172 grams per hour.

The embodiments of the invention in which an exclusive property or privilege is claimed are defined as follows:

1. A continuous distillation process for removal of light ends impurities some of which are substantially water soluble and some of which are substantially water insoluble, from a crude alkyl ester of a carboxylic acid of the formula $R_1COOR_2$ wherein $R_1$ is hydrogen, an alkyl group of 1 to 5 carbons, or an alkenyl group of 1 to 5 carbons, and wherein $R_2$ is an alkyl group of 1 to 3 carbons, said crude ester containing from about 0.1 to 5% by weight of light end impurities, which process comprises continuously;
   a. passing said crude ester as feed to a distillation zone which is operated so as to obtain a residue consisting of the said ester having less of said light ends impurities therein than said crude ester, and so as to obtain a distillate of overhead vapors containing light ends impurities;
   b. adding to said overhead vapors an inert gas and water to give a combined overhead stream, said inert gas being added in an amount of at least 1.0 milliliter, as measured at standard temperature and pressure, of said inert gas per gram of said feed to the distillation tower, and wherein the amount of water added to said overhead vapors is from about 0.5 to 50% by weight of that of said feed;
   c. in a partial condenser cooling the combined stream so obtained by adding said inert gas and said water to said overhead vapors to a temperature sufficient to condense substantially all of the water and the said ester contained therein, but which temperature is high enough to cause the amount of the substantially water insoluble light ends impurities contained in the hereafter defined vapor phase of the hereafter defined phase separator to be at least 50% of the amount of said water insoluble light ends impurities contained in said feed to the distillation zone; and
   d. passing the effluent from said partial condenser to a phase separator and allowing said effluent to separate into a vapor phase, a liquid aqueous phase and a liquid ester phase, and recycling said liquid ester phase back to the top of said distillation zone as reflux.

2. The process of claim 1 wherein said distillation zone contains the equivalent of at least about 15 theoretical trays.

3. The process of claim 1 wherein said light ends impurities consist substantially of ethyl acetate, ethyl alcohol, diethyl ether and sulfur dioxide.

4. The process of claim 1 wherein said distillation zone and said partial condenser are operated at substantially atmospheric pressure and the combined stream passed to said partial condenser is cooled to a temperature within the range of 10° to 50°C.

5. The process of claim 1 wherein said substantially water insoluble light ends impurities comprise dialkyl ethers and said substantially water soluble impurities comprise alkyl alcohols, the alkyl portions of which ethers and alcohols correspond to the alcohol moiety portion of said ester.

6. The process of claim 5 wherein $R_1$ is an alkenyl group.

7. A continuous distillation process for removal of light ends impurities, some of which are substantially water insoluble and comprise diethyl ether and ethyl acetate and some of which are substantially water soluble and comprise ethyl alcohol, from crude ethyl acrylate which contains from about 0.1 to 5.0% by weight of said light ends impurities which process comprises continuously:
- a. passing said crude ethyl acrylate as feed to a distillation zone which is operated so as to obtain a residue consisting of ethyl acrylate having less of said light ends impurities therein than said crude ethyl acrylate, and so as to obtain a distillate of overhead vapors containing light ends impurities;
- b. adding to said overhead vapors an inert gas and water said inert gas being added in an amount of at least 1.0 milliliter, as measured at standard temperature and pressure, of said inert gas per gram of said feed to the distillation zone, and wherein the amount of water added to said overhead vapors is from about 0.5 to 50% by weight of that of said feed;
- c. in a partial condenser cooling the combined stream so obtained by said adding of said inert gas and said water to said overhead vapors to a temperature sufficient to condense substantially all of the water and ethyl acrylate contained therein, but which temperature is high enough to cause the amount of the substantially water insoluble light ends impurities contained in the hereafter defined vapor phase of the hereafter defined phase separator to be at least 50% of the amount of said water insoluble light ends impurities contained in said feed to the distillation zone; and
- d. passing the effluent from said partial condenser to a phase separator and allowing such to separate into a vapor phase, a liquid aqueous phase and a liquid ester phase, and recycling said liquid ester phase back to the top of said distillation zone as reflux.

8. The process of claim 1 wherein said distillation zone is operated at a pressure within the range of about 0.5 to 2.0 atmospheres absolute.

9. The process of claim 8 wherein a blowdown of said liquid ester phase is taken at least periodically.

10. The process of claim 7 wherein said crude ethyl acrylate is derived from the interaction of ethylene and acrylic acid in the presence of sulfuric acid and contains sulfur dioxide.

11. The process of claim 10 wherein said distillation zone contains the equivalent of at least 15 theoretical trays and is operated at a pressure within the range of 0.5 to 2.0 atmospheres absolute; wherein the amount of inert gas added to said overhead vapors comprises from 5 to 15 milliliters, as measured at standard temperature and pressure, per gram of said feed; and wherein the amount of water added to said overhead vapors is from 1 to 10% by weight of that of said feed.

* * * * *